United States Patent [19]

Miyano et al.

[11] Patent Number: 4,605,662

[45] Date of Patent: Aug. 12, 1986

[54] 1-SUBSTITUTED PYRROLIZIDINE DERIVATIVES AND ANTIARRHYTHMIC USE THEREOF

[75] Inventors: Seiji Miyano, Fukuoka; Kunihiro Sumoto, Ohnojo; Fumio Satoh, Nagaokakyo; Hidetsura Cho, Ibaraki, all of Japan

[73] Assignee: Suntory Ltd., Osaka, Japan

[21] Appl. No.: 529,548

[22] Filed: Sep. 6, 1983

[30] Foreign Application Priority Data

Sep. 9, 1982 [JP] Japan ............................... 57-157819

[51] Int. Cl.⁴ .................... C07D 487/04; A61K 31/40
[52] U.S. Cl. ...................................... 514/413; 548/453
[58] Field of Search ................ 548/453; 424/274; 514/413

[56] References Cited

U.S. PATENT DOCUMENTS 3,544,590 12/1970 Kittleson et al. .................. 578/453
4,213,983 7/1980 Hadley et al. ..................... 548/453

OTHER PUBLICATIONS

Pizzorno et al., J. Org. Chem., 39, p. 731 (1974).

*Primary Examiner*—Richard L. Raymond
*Assistant Examiner*—D. B. Springer
*Attorney, Agent, or Firm*—Burgess, Ryan & Wayne

[57] ABSTRACT

A novel 1-substituted pyrrolizidine derivative having the formula:

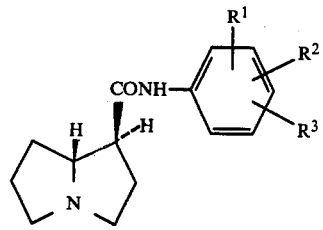

(wherein $R^1$ is hydrogen or a lower alkyl group; $R^2$ is hydrogen, a lower alkyl or lower alkoxy group, or a halogen; $R^3$ is hydrogen, a lower alkyl, lower alkoxy or amino group, or a halogen), which can be produced by reacting 1-chlorocarbonyl (or alkoxycarbonyl)pyrrolizidine with a corresponding substituted aniline (or an alkali metal salt thereof). The pyrrolizidine derivative has antiarrhythmic activity.

10 Claims, No Drawings

1-SUBSTITUTED PYRROLIZIDINE DERIVATIVES AND ANTIARRHYTHMIC USE THEREOF

The present invention relates to novel 1-substituted pyrrolizidine derivatives and to the use thereof.

Thus, the present invention is directed to 1-substituted pyrrolizidine derivatives represented by the following formula:

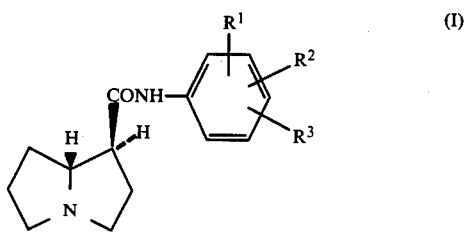

(wherein $R^1$ is hydrogen or a lower alkyl group; $R^2$ is hydrogen, a lower alkyl or lower alkoxy group, or a halogen; $R^3$ is hydrogen, a lower alkyl, lower alkoxy or amino group, or a halogen) and to an antiarrhythmic agent composed of the above-mentioned derivative.

The compounds of the formula (I) can be prepared, as shown by the scheme given below and according to the methods presented in the following, from 1-alkoxycarbonylpyrrolizidines (II) obtainable in accordance with the procedure described in the literature (M. T. Pizzorno and S. M. Albonico, J. Org. Chem., 39, 731 (1974)) and a variety of substituted aniline derivatives.

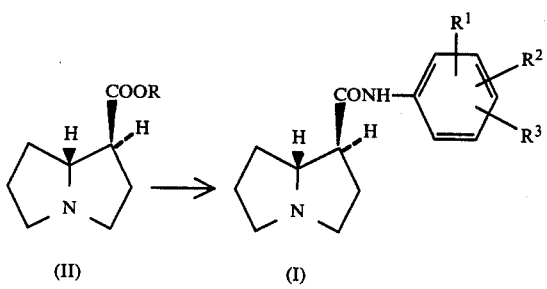

(wherein R is a methyl or ethyl group; $R^1$, $R^2$ and $R^3$ each are as defined hereinbefore).

Method A

A compound of the formula (I) can be prepared by subjecting a 1-alkoxycarbonylpyrrolizidine (II) to hydrolysis with a mineral acid such as hydrochloric acid to form a free carboxylic acid and then allowing a halogenating agent such as thionyl chloride to act on said free carboxylic acid to yield an acid halide, which is allowed to react with a corresponding substituted aniline. The reaction is preferably conducted in a solvent (e.g., chloroform, etc.) which is capable of dissolving the acid halide but does not interfere with the reaction. The reaction may be promoted by adding to the reaction system an inorganic base such as alkali hydroxides or an organic amine such as triethylamine and pyridine, but the reaction proceeds without the use of bases.

Method B

A compound of the formula (I) can be also produced by allowing a 1-alkoxycarbonylpyrrolizidine (II) to react with an alkali metal salt of a corresponding substituted aniline. The above-mentioned alkali metal salt can be formed by allowing an alkali metal compound such as sodium hydroxide, sodium amide and butyl lithium to act on one of various substituted anilines in an anhydrous solvent such as ether, tetrahydrofurane, dioxane and benzene.

In the above methods A and B, use of, as the substituted aniline, lower-alkylanilines, lower-alkoxyanilines, halogenoanilines and aminoanilines gives corresponding N-(substituted phenyl)-1-pyrrolizidinecarboxamides, respectively.

The N-(substituted phenyl)-1-pyrrolizidinecarboxamide derivatives thus obtained are novel compounds and have antiarrhythmic activity as described below.

Antiarrhythmic activity

In accordance with the method described by J. W. Lawson (Journal of Pharmacology and Experimental Therapeutics, vol. 160, pp. 22, 1968), male mice of the ddy strain weighing 16 to 30 g were allowed to inhale chloroform to induce ventricular arrhythmias. At the time when they ceased to breathe, the electrocardiogram of each animal was recorded to observe the ventricular flutter and fibrillation. The abnormalities of the ventricles observed in these animals can be prevented by pretreatment with substances which have antiarrhythmic activity. The compounds of this invention were subcutaneously injected in 4-5 different doses to groups of 29 to 40 mice. Thirty minutes later, the mice were subjected to inhalation of chloroform to induce arrhythmias, and the protection by each dose against the ventricular flutter and fibrillation were expressed as percent. The 50% effective dose ($ED_{50}$) and its 95% confidence limits were determined according to the method of Litchfield and Wilcoxon (Journal of Pharmacology and Experimental Therapeutics, vol. 96, pp. 99, 1949), as shown in Table 1.

The 50% lethal doses (median lethal doses, $LD_{50}$) were computed by the "Up and Down Method" (Pharmacological Experiment, compiled by Takagi and Ozawa, pp. 204, Nanzando, 1972) using male mice of the ddy strain weighing 18 to 22 g, and the ratios of the $LD_{50}$ to $ED_{50}$ values were expressed as the therapuetic indices, as presented in Table 1.

TABLE 1

Antiarrhythmic activity

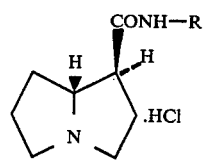

| Compound Number | R | $ED_{50}$, mg/kg (95% confidence limits) | $LD_{50}$ mg/kg | Therapeutic index |
|---|---|---|---|---|
| I | Me- | >100 100 ($ED_{20}$) | >500 | |
| II | MeO- | 74 (57.1-95.8) | >500 | |

TABLE 1-continued

Antiarrhythmic activity

Structure: bicyclic pyrrolizidine with CONH-R substituent, ·HCl salt

| Compound Number | R | ED$_{50}$, mg/kg (95% confidence limits) | LD$_{50}$ mg/kg | Therapeutic index |
|---|---|---|---|---|
| III | 3-MeO-C$_6$H$_4$ | >100, 100 (ED$_{40}$) | >500 | |
| IV | 4-MeO-C$_6$H$_4$ | >100, 100 (ED$_{20}$) | >500 | |
| V | 2-Cl-C$_6$H$_4$ | >100, 100 (ED$_{50}$) | 263 | |
| VI | 2-Br-C$_6$H$_4$ | >100, 100 (ED$_{40}$) | >500 | |
| VII | 2,3-diMe-C$_6$H$_3$ | >100, 100 (ED$_{20}$) | >500 | |
| VIII | 2,5-diMe-C$_6$H$_3$ | >100, 100 (ED$_{20}$) | >500 | |
| IX | 2,3-diMe-C$_6$H$_3$ | 29 (17.0–49.6) | 447 | 15.4 |
| X | 3,5-diMe-C$_6$H$_3$ | 100, >100 (ED$_{20}$) | >500 | |
| XI | 2,6-diEt-C$_6$H$_3$ | 38 (30–48) | 244 | 6.24 |
| XII | 2,5-diMeO-C$_6$H$_3$ | >100, 100 (ED$_{40}$) | >500 | |
| XIII | 2,5-diCl-C$_6$H$_3$ | 38 (26–56) | 263 | 6.92 |
| XIV | 2,5-diBr-C$_6$H$_3$ | 43 (32–58) | 468 | 10.88 |
| XV | 2,3,5-triMe-C$_6$H$_2$ | >100, 100 (ED$_{20}$) | 394 | |

The effective dose of an antiarrhythmic agent varies depending upon the method of administration, type and seriousness of arrhythmias and physical conditions of patients, but in general, the agent is administered in an amount sufficient for causing dysrhythmias to revert to normal sinus rhythm. With reference to the compounds of this invention, they are normally administered orally in a daily dose of 50 to 200 mg per adult, 3 to 4 times daily, or by intravenous drip injection in a daily dose of 0.5 to 5 mg/kg of body weight.

EXAMPLE

General production process in the example

In dioxane is dissolved 1.5 to 2 equivalents of each of various substituted anilines, and 1.5 to 2 equivalents of sodium hydride is added to the solution at room temperature under a stream of nitrogen, with stirring. The mixture is heated at 100° C. for 2 hours and then cooled at room temperature, followed by adding dropwise a solution of an equivalent of 1-ethoxycarbonylpyrrolizidine in dioxane. After the dropwise addition, the reaction mixture is again heated at 100° C. for 2 hours and then cooled. Ice and ether are added to the reaction mixture under ice-cooling, followed by extracting with 5% aqueous hydrochloric acid. The resulting hydrochloric acid layer is neutralized with sodium hydrogencarbonate and then washed with ether. The remaining aqueous layer is made alkaline with a 20% aqueous sodium hydroxide solution, followed by extracting with chloroform. The resulting chloroform layer is washed with saturated aqueous sodium chloride solution, dried over magnesium sulfate and freed of the solvent under reduced pressure. The resultant residue is made into a hydrochloride form in accordance with a conventional method, followed by recrystallization from ethanol-ether.

In accordance with the above-described general production process, and by employing as substituted anilines aniline, 2-methylaniline, 2-methoxyaniline, 3-methoxyaniline, 4-methoxyaniline, 2-aminoaniline, 2-fluoroaniline, 2-chloroaniline, 2-bromoaniline, 2,3-dimethylaniline, 2,4-dimethylaniline, 2,5-dimethylaniline, 2,6-dimethylaniline, 3,4-dimethylaniline, 3,5-dimethylaniline, 2,6-diethylaniline, 2,5-dimethoxyaniline, 2,6-dichloroaniline, 2,6-dibromoaniline and 2,4,6-trimethylaniline, there were obtained corresponding N-phenyl-1-pyrrolizidinecarboxamide, N-(2-methylphenyl)-1-pyrrolizidinecarboxamide, N-(2-methoxyphenyl)-1-pyrrolizidinecarboxamide, N-(3-methoxyphenyl)-1-pyrrolizidinecarboxamide, N-(4-methoxyphenyl)-1-pyrrolizidinecaeboxamide, N-(2-aminophenyl)-1-pyrrolizidinecarboxamide, N-(2-fluorophenyl)-1-pyrrolizidinecarboxamide, N-(2-chlorophenyl)-1-pyrrolizidinecarboxamide, N-(2-bromophenyl)-1-pyrrolizidinecarboxamide, N-(2,3-dimethylphenyl)-1-pyrrolizidinecarboxamide, N-(2,4-dimethylphenyl)-1-pyrrolizidinecarboxamide, N-(2,5-dimethylphenyl)-1-pyrrolizidinecarboxamide, N-(2,6-dimethylphenyl)-1-pyrrolizidinecarboxamide, N-(3,4-dimethylphenyl)-1-pyrrolizidinecarboxamide, N-(3,5-dimethylphenyl)-1-pyrrolizidinecarboxamide, N-(2,6-diethylphenyl)-1-pyrrolizidinecarboxamide, N-(2,5-dimethoxyphenyl)-1-pyrrolizidinecarboxamide, N-(2,6-dichlorophenyl)-1-pyrrolizidinecarboxamide, N-(2,6-dibromophenyl)-1-pyrrolizidinecarboxamide, N-(2,4,6-trimethylphenyl)-1-pyrrolizidinecarboxamide, respectively.

Typical physical properties of the 1-substituted pyrrolizidines thus obtained are shown in Table 2 in the same order as described above.

TABLE 2

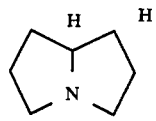

| Compound Number | R | m.p. °C. | Yield % | NMR (free base, CDCl$_3$) δ | Elemental analysis, % Theor. value | Exp. value |
|---|---|---|---|---|---|---|
| 1 | (phenyl) | 207–210 | 56 | 6.86–7.63(5H,m,arom. proton) | C$_{14}$H$_{19}$ClN$_2$O<br>C 63.03<br>H 7.18<br>N 10.50 | 62.98<br>7.21<br>10.37 |
| 2 | (2-Me-phenyl) | 176–181 | 66 | 2.10(3H,s,CH$_3$)<br>6.53–7.23(4H,m,arom. proton) | C$_{15}$H$_{21}$ClN$_2$O<br>C 64.16<br>H 7.13<br>N 9.98 | 64.07<br>7.73<br>9.89 |
| 3 | (2-MeO-phenyl) | 169–172 | 61 | 3.82(3H,s,OC$\underline{H}_3$)<br>6.63–7.33(4H,m,arom. proton) | C$_{15}$H$_{21}$ClN$_2$O$_2$<br>C 60.70<br>H 7.54<br>N 9.44 | 60.54<br>7.23<br>9.24 |
| 4 | (3-MeO-phenyl) | 129–134 | 61 | 3.67(3H,s,OC$\underline{H}_3$)<br>6.47–7.40(4H,m,arom. proton) | C$_{15}$H$_{21}$ClN$_2$O$_2$<br>C 60.70<br>H 7.13<br>N 9.44 | 60.56<br>7.32<br>9.13 |
| 5 | (4-OMe-phenyl) | Picrate 171.5–172.5 | 64 | 3.73(3H,s,OC$\underline{H}_3$)<br>6.74(2H,d,J = 10Hz,arom. proton)<br>7.37(2H,d,J = 10Hz,arom. proton) | Picrate C$_{21}$H$_{23}$N$_5$O$_9$<br>C 51.53<br>H 4.74<br>N 14.31 | 51.63<br>4.56<br>14.07 |
| 6 | (2-H$_2$N-phenyl) | Picrate 232–235 | 40 | 7.06–7.58(4H,m,arom. proton) | Picrate C$_{20}$H$_{22}$N$_6$O$_8$<br>C 50.63<br>H 4.67<br>N 17.72 | 50.34<br>4.73<br>17.56 |
| 7 | (2-F-phenyl) | Picrate 173.5–174.5 | 63 | 6.81–7.25(3H,m,arom. proton)<br>7.85–8.28(1H,m,arom. proton) | Picrate C$_{20}$H$_{20}$FN$_2$O$_8$<br>C 50.31<br>H 4.23<br>N 14.67 | 50.47<br>4.28<br>14.50 |

TABLE 2-continued

CONH—R on pyrrolizidine (H, H stereochem shown)

| Compound Number | R | m.p. °C. | Yield % | NMR (free base, CDCl₃) δ | Elemental analysis, % Theor. value | Exp. value |
|---|---|---|---|---|---|---|
| 8 | 2-Cl-phenyl | Picrate 168–168.5 | 45 | 6.92–7.34(3H,m,arom. proton) 8.20–8.40(1H,dd,J = 8.0, 2.5Hz,6'-position proton) | Picrate C₂₀H₂₀ClN₅O₈ C 48.64 H 4.08 N 14.18 | 48.49 4.07 14.13 |
| 9 | 2-Br-phenyl | Picrate 120–121 | 60 | 6.80–7.52(3H,m,arom. proton) 8.10–8.34(1H,dd,J = 6.0, 2.0Hz,6'-position proton) | Picrate C₂₀H₂₀BrN₂O₈ C 44.62 H 3.75 N 13.01 | 44.82 3.75 12.95 |
| 10 | 2,3-diMe-phenyl | 211–213 | 65 | 2.08(3H,s,CH₃) 2.24(3H,s,CH₃) 6.86–7.50(3H,m,arom. proton) | C₁₆H₂₃ClN₂O C 65.18 H 7.86 N 9.50 | 64.86 7.86 9.51 |
| 11 | 3,4-diMe-phenyl | Picrate 169–170 | 61 | 2.18(3H,s,CH₃) 2.25(3H,s,CH₃) 6.82–7.92(3H,m,arom. proton) | Picrate C₂₂H₂₅N₅O₈ C 54.20 H 5.17 N 14.37 | 54.27 5.13 14.30 |
| 12 | 2,5-diMe-phenyl | Picrate 159–160.5 | 67 | 2.19(3H,s,CH₃) 2.29(3H,s,CH₃) 6.78–7.98(3H,m,arom. proton) | Picrate C₂₂H₂₅N₅O₈ C 54.20 H 5.17 N 14.37 | 54.03 5.12 14.23 |
| 13 | 2,6-diMe-phenyl | 189–191 | 81 | 2.03(6H,s,2xCH₃) 6.93(3H,s,arom. proton) | C₁₆H₂₃ClN₂O C 65.18 H 7.86 N 9.50 | 65.00 7.82 9.49 |
| 14 | 3,4-diMe-phenyl (alt substitution) | Picrate 181.5–183 | 60 | 2.16(6H,s,2xCH₃) 6.72–7.34(3H,m,arom. proton) | Picrate C₂₂H₂₅N₅O₈ C 54.20 H 5.17 N 14.37 | 54.17 5.11 14.28 |
| 15 | 3,5-diMe-phenyl | Picrate 172–173 | 59 | 2.25(6H,s,2xCH₃) 6.69(1H,br.s,4'-position proton) 7.12(2H,br.s,2',6'-position protons) | Picrate C₂₂H₂₅N₅O₈ C 54.20 H 5.17 N 14.37 | 54.48 5.07 14.26 |

TABLE 2-continued

CONH—R

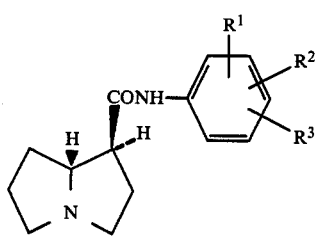

| Compound Number | R | m.p. °C. | Yield % | NMR (free base, CDCl₃) δ | Elemental analysis, % Theor. value | Exp. value |
|---|---|---|---|---|---|---|
| 16 | 2,6-Et,Et-phenyl | Picrate 124.5-126 | 80 | 1.04(6H,t,J = 7.0Hz,2xCH₂C$H_3$) 2.83(4H,q,J = 7.0Hz,2xC$H_2$CH₃) 6.80-7.10(3H,m,arom. proton) | Picrate $C_{24}H_{29}N_5O_8$ C 55.91 H 5.67 N 13.59 | 55.54 5.78 13.38 |
| 17 | 2-MeO,4-OMe-phenyl | Picrate 160-162 | 35 | 3.75(3H,s,OC$H_3$) 3.81(3H,s,OC$H_3$) 6.50(1H,dd,J = 9.0,2.5Hz, 4'-position proton) 6.76(1H,d,J = 9.0Hz,2'-position proton) 8.08(1H,d,J = 2.5Hz,6'-position proton) | Picrate $C_{22}H_{25}N_5O_{10}$ C 50.36 H 4.85 N 13.48 | 50.67 4.86 13.22 |
| 18 | 2,6-Cl,Cl-phenyl | Picrate 222.5-224 | 63 | 7.02(1H,dd,J = 10.0,5.0Hz, 4'-position proton) 7.23(1H,d,J = 5.0Hz,3'-position proton) 7.29(1H,d,J = 10.0Hz,5'-position proton) | Picrate $C_{20}H_{19}Cl_2N_5O_8$ C 45.45 H 3.60 N 13.26 | 45.53 3.69 13.10 |
| 19 | 2,6-Br,Br-phenyl | Free base 194-197 | 52 | 6.89(1H,dd,J = 9.0,7.5Hz, 4'-position proton) 7.47(1H,d,J = 7.5Hz,3'-position proton) 7.48(1H,d,J = 9.0Hz,5'-position proton) | Free base $C_{14}H_{16}Br_2N_2O$ C 43.32 H 4.16 N 7.22 | 43.27 4.16 7.30 |
| 20 | 2,4,6-Me,Me,Me-phenyl | Picrate 218-220 | 59 | 2.10(6H,s,2xC$H_3$) 2.21(3H,s,C$H_3$) | Picrate $C_{23}H_{27}N_5O_8$ C 55.09 H 5.39 N 13.97 | 54.86 5.36 13.80 |

We claim:

1. A 1-substituted pyrrolizidine compound of the formula:

(wherein $R^1$ is hydrogen or a lower alkyl group; $R^2$ is hydrogen, a lower alkyl or lower alkoxy group, or a halogen; $R^3$ is hydrogen, a lower alkyl, lower alkoxy or amino group, or a halogen).

2. A compound according to claim 1 wherein $R^1$ and $R^2$ each are hydrogen; $R^3$ is a methyl, methoxy or amino group, or chlorine or bromine.

3. A compound according to claim 1 wherein $R^1$ is hydrogen; $R^2$ and $R^3$ each are a methyl, ethyl or methoxy group, or chlorine.

4. A compound according to claim 1 wherein $R^1$, $R^2$ and $R^3$ each are a methyl group.

5. A compound according to claim 1, selected from the group consisting of;
N-Phenyl-1-pyrrolizidinecarboxamide,
N-(2-methylphenyl)-1-pyrrolizidinecarboxamide,
N-(2-methoxyphenyl)-1-pyrrolizidinecarboxamide,
N-(3-methoxyphenyl)-1-pyrrolizidinecarboxamide,
N-(4-methoxyphenyl)-1-pyrrolizidinecarboxamide,
N-(2-aminophenyl)-1-pyrrolizidinecarboxamide,
N-(2-fluorophenyl)-1-pyrrolizidinecarboxamide,
N-(2-chlorophenyl)-1-pyrrolizidinecarboxamide,
N-(2-bromophenyl)-1-pyrrolizidinecarboxamide, N-(2,3-dimethylphenyl)-1-pyrrolizidinecarboxamide,
N-(2,4-dimethylphenyl)-1-pyrrolizidinecarboxamide,
N-(2,5-dimethylphenyl)-1-pyrrolizidinecarboxamide,
N-(2,6-dimethylphenyl)-1-pyrrolizidinecarboxamide,
N-(3,4-dimethylphenyl)-1-pyrrolizidinecarboxamide,
N-(3,5-dimethylphenyl)-1-pyrrolizidinecarboxamide,
N-(2,6-diethylphenyl)-1-pyrrolizidinecarboxamide,
N-(2,5-dimethoxyphenyl)-1-pyrrolizodinecarboxamide,
N-(2,6-dichlorophenyl)-1-pyrrolizidinecarboxamide,
N-(2,6-dibromophenyl)-1-pyrrolizidinecarboxamide and
N-(2,4,6-trimethylphenyl)-1-pyrrolizidinecarboxamide.

6. A pharmaceutical composition useful for providing an antiarrhythmic effect, said composition comprised of an antiarrhythmic effective amount of a 1-substituted pyrrolizidine compound of the formula:

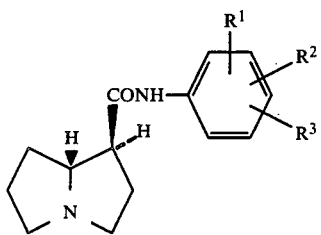

(wherein $R^1$ is hydrogen or a lower alkyl group; $R^2$ is hydrogen, a lower alkyl or alkoxy group, or a halogen; $R^3$ is hydrogen, a lower alkyl, lower alkoxy or amino group, or a halogen) and a pharmaceutical acceptable carrier.

7. The pharmaceutical composition of claim 6 wherein said compound is selected from the group consisting of:
N-Phenyl-1-pyrrolizidinecarboxamide,
N-(2-methylphenyl)-1-pyrrolizidinecarboxamide,
N-(2-methoxyphenyl)-1-pyrrolizidinecarboxamide,
N-(3-methoxyphenyl)-1-pyrrolizidinecarboxamide,
N-(4-methoxyphenyl)-1-pyrrolizidinecarboxamide,
N-(2-aminophenyl)-1-pyrrolizidinecarboxamide,
N-(2-fluorophenyl)-1-pyrrolizidinecarboxamide,
N-(2-chlorophenyl)-1-pyrrolizidinecarboxamide,
N-2-bromophenyl)-1-pyrrolizidinecarboxamide,
N-(2,3-dimethylphenyl)-1-pyrrolizidinecarboxamide,
N-(2,4-dimethylphenyl)-1-pyrrolizidinecarboxamide,
N-(2,5-dimethylphenyl)-1-pyrrolizidinecarboxamide,
N-(2,6-dimethylphenyl)-1-pyrrolizidinecarboxamide,
N-(3,4-dimethylphenyl)-1-pyrrolizidinecarboxamide,
N-(3,5-dimethylphenyl)-1-pyrrolizidinecarboxamide,
N-(2,6-diethylphenyl)-1-pyrrolizidinecarboxamide,
N-(2,5-dimethoxyphenyl)-1-pyrrolizidinecarboxamide,
N-(2,6-dichlorophenyl)-1-pyrrolizidinecarboxamide,
N-(2,6-dibromophenyl)-1-pyrrolizidinecarboxamide,
N-(2,4,6-trimethylphenyl)-1-pyrrolizidinecarboxamide.

8. A method of inhibiting arrhythmias in a host afflicted with such arrhythmias, which comprises administering to said host an antiarrhythmic effective amount of the pharmaceutical composition of claim 6.

9. A method of inhibiting arrhythmias in a host afflicted with such arrhythmias, which comprises administering to said host an antiarrhythmic effective amount of the pharmaceutical composition of claim 7.

10. The method of claim 8 wherein said pharmaceutical composition is administered in a daily dose of 0.5 to 5 mg/kg of host body weight.

* * * * *